United States Patent
Dlugos et al.

(10) Patent No.: US 7,879,068 B2
(45) Date of Patent: Feb. 1, 2011

(54) FEEDBACK SENSING FOR A MECHANICAL RESTRICTIVE DEVICE

(75) Inventors: Daniel F. Dlugos, Middletown, OH (US); Amy L. Poeppelman, Mason, OH (US); Janna M. Burrell, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 719 days.

(21) Appl. No.: 11/683,671

(22) Filed: Mar. 8, 2007

(65) Prior Publication Data

US 2007/0167672 A1     Jul. 19, 2007

Related U.S. Application Data

(63) Continuation-in-part of application No. 11/036,460, filed on Jan. 14, 2005, now Pat. No. 7,601,162, and a continuation-in-part of application No. 11/369,531, filed on Mar. 7, 2006.

(51) Int. Cl.
*A61B 17/12* (2006.01)

(52) U.S. Cl. ...................................... 606/201; 606/157

(58) Field of Classification Search ................. 606/151, 606/157, 201–204, 204.15; 600/37; 623/23.65
See application file for complete search history.

(56) References Cited

U.S. PATENT DOCUMENTS

| | | | |
|---|---|---|---|
| 3,570,495 A | 3/1971 | Wright | |
| 3,840,018 A | 10/1974 | Heifetz | |
| 4,201,218 A | 5/1980 | Feldman et al. | |
| 4,256,094 A | 3/1981 | Kapp et al. | |
| 4,592,339 A | 6/1986 | Kuzmak et al. | |
| 4,634,443 A | 1/1987 | Haber | |
| 4,702,235 A | 10/1987 | Hong | |

(Continued)

FOREIGN PATENT DOCUMENTS

EP       1 547 549       6/2005

(Continued)

OTHER PUBLICATIONS

European Search Report, dated May 3, 2006, for EP Application No. 06250156.4.

(Continued)

*Primary Examiner*—Anhtuan T Nguyen
*Assistant Examiner*—Ryan J Severson
(74) *Attorney, Agent, or Firm*—Frost Brown Todd LLC

(57) ABSTRACT

An apparatus comprises an implantable mechanically adjustable band configured to form a restriction in a patient. The band defines an inner diameter. The mechanical adjustability of the band is configured to permit the inner diameter defined by the band to be selectively varied. The apparatus further comprises an adjustment mechanism in communication with the band. The adjustment mechanism is operable to provide the mechanical adjustability of the band. The apparatus further comprises a sensor in communication with one or both of the mechanically adjustable band or the adjustment mechanism. The sensor is configured to sense a physical parameter associated with operation of the band. The physical parameter sensed by the sensor varies with the inner diameter defined by the band. The band may be used as a gastric band, among other potential uses.

19 Claims, 12 Drawing Sheets

U.S. PATENT DOCUMENTS

| | | |
|---|---|---|
| 4,898,585 A | 2/1990 | Borsanyi et al. |
| 5,241,965 A | 9/1993 | Mick |
| 5,383,893 A | 1/1995 | Daneshvar |
| 5,449,368 A | 9/1995 | Kuzmak |
| 5,938,669 A | 8/1999 | Klaiber et al. |
| 6,067,991 A | 5/2000 | Forsell |
| 6,210,347 B1 | 4/2001 | Forsell |
| 6,432,040 B1 | 8/2002 | Meah |
| 6,461,292 B1 | 10/2002 | Forsell |
| 6,470,892 B1 | 10/2002 | Forsell |
| 6,478,745 B2 | 11/2002 | Nakagawa et al. |
| 6,485,462 B1 | 11/2002 | Kriesel |
| 6,547,801 B1 | 4/2003 | Dargent et al. |
| 6,709,385 B2 * | 3/2004 | Forsell ................ 600/29 |
| 6,855,115 B2 | 2/2005 | Fonseca et al. |
| 7,351,240 B2 | 4/2008 | Hassler, Jr. et al. |
| 7,374,565 B2 | 5/2008 | Hassler, Jr. et al. |
| 7,390,294 B2 | 6/2008 | Hassler, Jr. et al. |
| 7,442,165 B2 | 10/2008 | Forsell |
| 7,481,763 B2 | 1/2009 | Hassler, Jr. et al. |
| 2001/0011543 A1 * | 8/2001 | Forsell ................ 128/899 |
| 2003/0105385 A1 | 6/2003 | Forsell |
| 2003/0136417 A1 | 7/2003 | Fonseca et al. |
| 2004/0260319 A1 | 12/2004 | Egle |
| 2004/0267377 A1 | 12/2004 | Egle |
| 2005/0143765 A1 | 6/2005 | Bachmann et al. |
| 2005/0143766 A1 | 6/2005 | Bachmann et al. |
| 2006/0189888 A1 | 8/2006 | Hassler, Jr. et al. |
| 2006/0199997 A1 | 9/2006 | Hassler, Jr. et al. |
| 2006/0211912 A1 | 9/2006 | Dlugos et al. |
| 2006/0211913 A1 | 9/2006 | Dlugos et al. |
| 2006/0247722 A1 | 11/2006 | Maschino et al. |
| 2008/0221598 A1 | 9/2008 | Dlugos et al. |

FOREIGN PATENT DOCUMENTS

| | | |
|---|---|---|
| EP | 1 600 120 | 11/2005 |
| EP | 1 681 041 | 7/2006 |
| EP | 1 704 833 | 9/2006 |
| EP | 1 832 253 | 9/2007 |
| EP | 1 967 168 | 9/2008 |
| GB | 1 486 822 | 9/1977 |
| GB | 1486822 | 9/1977 |
| GB | 1486833 | 9/1977 |
| WO | WO 01/51108 | 7/2001 |
| WO | WO 03/061504 | 7/2003 |
| WO | WO 03/105732 | 12/2003 |

OTHER PUBLICATIONS

Examination Report dated Feb. 20, 2007 for Application No. 06250156.

Partial EPO Search Report dated Jan. 13, 2009 for Application No. 08250782.

Extended EPO Search Report dated Apr. 22, 2009 for Application No. 08250782.

* cited by examiner

US 7,879,068 B2

FEEDBACK SENSING FOR A MECHANICAL RESTRICTIVE DEVICE

PRIORITY

This application is a continuation-in-part of prior co-pending U.S. Non-Provisional application Ser. No. 11/036,460, filed Jan. 14, 2005, entitled "Actuator for an Implantable Band," and published as U.S. Pub. No. 2006/0161186, the disclosure of which is incorporated by reference herein. This application is also a continuation-in-part of prior co-pending U.S. Non-Provisional application Ser. No. 11/369,531, filed Mar. 7, 2006, entitled "Non-Invasive Pressure Measurement In a Fluid Adjustable Restrictive Device," and published as U.S. Pub. No. 2006/0211913, the disclosure of which is incorporated by reference herein.

BACKGROUND

Many devices and methods for treating obesity have been made and used, including but not limited to adjustable gastric bands. An example of such an adjustable gastric band is disclosed in U.S. Pat. No. 6,067,991, entitled "Mechanical Food Intake Restriction Device," which issued on May 30, 2000, and which is incorporated herein by reference. Gastric bands may be provided as fluid-based devices or as mechanical devices, among other types, including combinations thereof. Exemplary fluid-based gastric band devices are disclosed in U.S. Pat. No. 4,592,339, entitled "Gastric Banding Device," which issued on Jun. 3, 1986, and which is incorporated herein by reference. Exemplary mechanical gastric band devices are disclosed in U.S. Pub. No. 2005/0143766, entitled "Telemetrically Controlled Band for Regulating Functioning of a Body Organ or Duct, and Methods of Making, Implantation and Use," which published on Jun. 30, 2005, and which is incorporated herein by reference. Exemplary mechanical gastric band devices are also disclosed in U.S. Provisional Application Ser. No. 60/530,497, filed Dec. 17, 2003, which is incorporated herein by reference.

Those of ordinary skill in the art will appreciate that it may be advantageous in certain circumstances to sense pressure, strain, or other parameters associated with operation of a gastric band device. For instance, various devices and techniques for pressure data acquisition and processing for fluid-based gastric band systems are disclosed in U.S. Non-Provisional application Ser. No. 11/065,410, filed Feb. 24, 2005, entitled "Device for Non-Invasive Measurement of Fluid Pressure in an Adjustable Restriction Device," and published as U.S. Pub. No. 2006/0189888; U.S. Non-Provisional application Ser. No. 11/369,531, filed Mar. 7, 2006, entitled "Non-Invasive Pressure Measurement in a Fluid Adjustable Restrictive Device," and published as U.S. Pub. No. 2006/0211913; and U.S. Non-Provisional application Ser. No. 11/398,940, filed Apr. 6, 2006, entitled "Monitoring of a Food Intake Restriction Device," and published as U.S. Pub. No. 2006/0199997. The disclosure of each of those applications and publications is incorporated by reference herein. Such parameter data may be obtained before, during, and/or after adjustment of a gastric band, and may be useful for adjustment, diagnostic, monitoring, or other purposes, and may be obtained with respect to a mechanical gastric band. The foregoing examples are merely illustrative and not exhaustive. While a variety of techniques and devices have been used to treat obesity, it is believed that no one prior to the inventors has previously made or used an invention as described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

Reference will now be made in detail to the present preferred embodiment of the invention, an example of which is illustrated in the accompanying drawings.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

Figure 1:
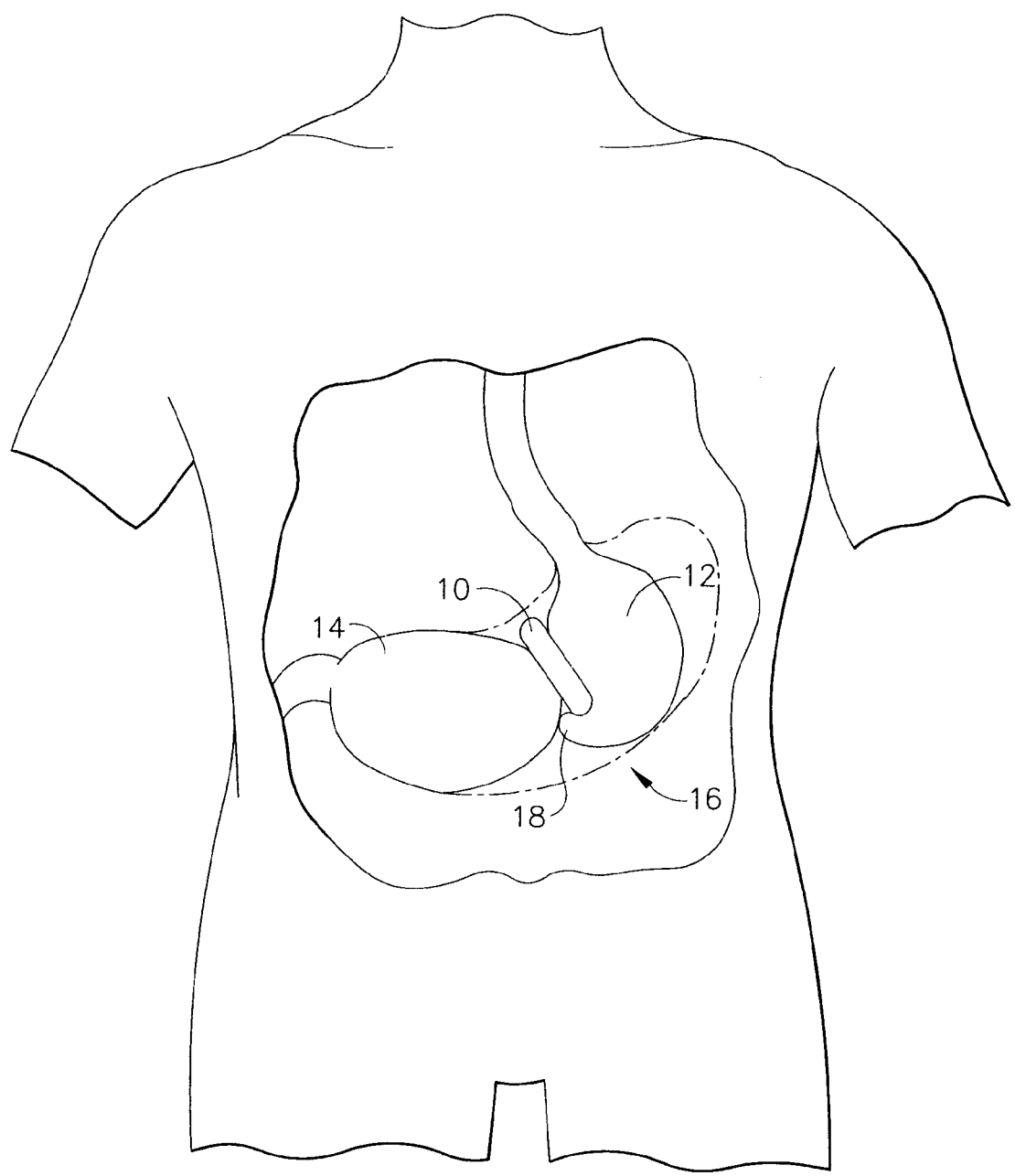
FIG. 1 is a diagrammatic environmental view of an exemplary gastric band wrapped around an upper part of a stomach.

Referring to FIG. 1, an exemplary adjustable gastric band 10 forms an adjustable stoma between upper portion 12 and lower portion 14 of a patient's stomach 16. Of course, band 10 may be positioned at a variety of alternative locations, including but not limited to at or near the gastro-esophageal junction of the patient. In the present example, band 10 is kept in place by attaching its two ends together and extending portion 18 of stomach 16 over the adjustable gastric band 10 by suturing portion 18 to stomach 16. The stoma may be adjusted by varying the effective inner perimeter (which may also referred to as inner diameter, although the shape is not necessarily a circle) of band 10. An actuator is associated with band 10 to vary the inner perimeter. The actuating device may be integral with the band 10 itself or be external thereto.

FIGS. 2-5 illustrate an exemplary adjustable band 148 that includes actuators 150 and 152. Since actuators 150 and 152 are identical to each other in this particular example, only actuator 150 will be discussed. Of course, actuators 150 and 152 need not be identical, and may have any suitable number or types of differences. In the present example, actuator 150 is actuated by an increase of pressure within its internal cavity. But instead of relying on an external source of fluid pressure, actuator 150 is filled with a two phase medium, such as a propellant. For example, Vertrel CF may be used. Thus, an injection port and a bidirectional infuser are unnecessary. Alternatively, an injection port, infuser, or other device may be incorporated if desired.

In order to effect the phase change and expansion of the propellant, thermal element 154 (156 for actuator 152) is disposed adjacent actuator 150. In the embodiment depicted, thermal element 154 is a thin film Kapton heater which is attached to a surface of actuator 150. Wires (not shown) extend from element 154, to a controller (not shown) for selectively applying an electrical signal to element 154. In the embodiment depicted, when energized, element 154 produces sufficient heat to warm the two phase medium within the internal cavity of actuator 150, causing the medium to begin changing phase from liquid to gas, thereby increasing the pressure within actuator 150. Actuator 150 is configured to change shape in response to this increase in internal pressure, with the change in shape adapted to vary the size of the stoma.

In the embodiment depicted, actuator 150 lengthens in response to an increase in pressure. A control may measure the change in capacitance of actuator 150 to determine its length. The self capacitance of actuator 150 may vary as it lengthens. Capacitance change may be detected by incorporating actuator 150 into an LC circuit, and the frequency variations of an AC signal in the circuit may be compared to a reference frequency to detect the amount of expansion. Other processing may be used in addition or in the alternative. Additionally, a self contained actuator, such as actuator 150, may be used in conjunction with any suitable band configuration, such as any other band described herein. In addition, any other type of actuator may be used in lieu of actuator 150, including but not limited to the various other types of actuators explicitly described herein relative to other gastric band embodiments. Accordingly, the term "actuator" should in no way be read as limited to actuator 150 as described herein with reference to FIGS. 2-5 or as shown in FIGS. 2-5.

The embodiment of band 148 depicted in FIGS. 2-5 includes a clutch mechanism configured to hold band 148 at a particular size unless acted upon by either actuator 150 or 152. Although any suitable clutch mechanism may be used, FIGS. 9-12 depict pawl 160 which engages ratchet member 162. Pawl 160 is rotatably supported about transverse pivot 164, which separates pawl into upper portion 166 and lower portion 168. Lower portion 168 terminates in an angle 170 which is shaped complementarily to engage notches 172 of ratchet member 162. First ends 150a and 152a of actuators 150 and 152 are attached to respective sides of upper portion 166 in any suitable manner. Alternatively, actuators 150 and 152 could be configured as a single member with two separate internal cavities, with pawl 160 being molded to the portion between the two internal cavities.

First ends of resilient members, depicted in the figures as springs 174 and 176, are attached to pawl 160 adjacent distal end 160a. Second ends of springs 174 and 176 are secured to shroud 178, which comprises first portion 148a of band 148, and which covers and contains actuators 150 and 152. Springs 174 and 176 maintain pawl 160 generally perpendicular to ratchet 162, which is carried by second portion 148b. Relative longitudinal movement between first portion 148a and second portion 148b effects the change in the size of opening 180, as can been seen in FIGS. 2 and 4. Springs 174 and 176 provide a counterbalanced load at distal end 160a of pawl 160 which, in the absence of a force exerted by extension of either actuator 150 or 152 due to actuation, is sufficient to maintain angle 170 engaged in one of notches 172 to prevent relative movement between first portion 148a and second portion 148b, maintaining the selected size of area 180.

Figure 4:
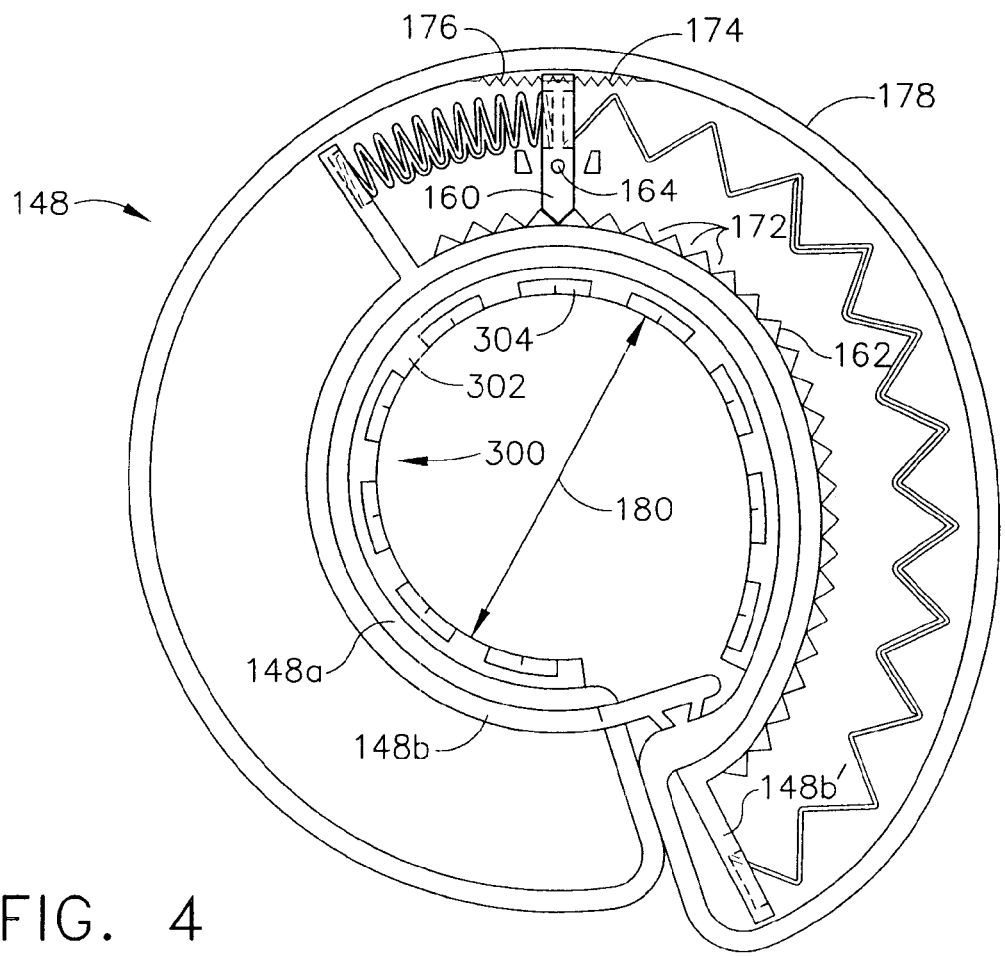
FIG. 4 is a plan view of the band of FIG. 2, depicting a minimum area configuration.
Figure 5:
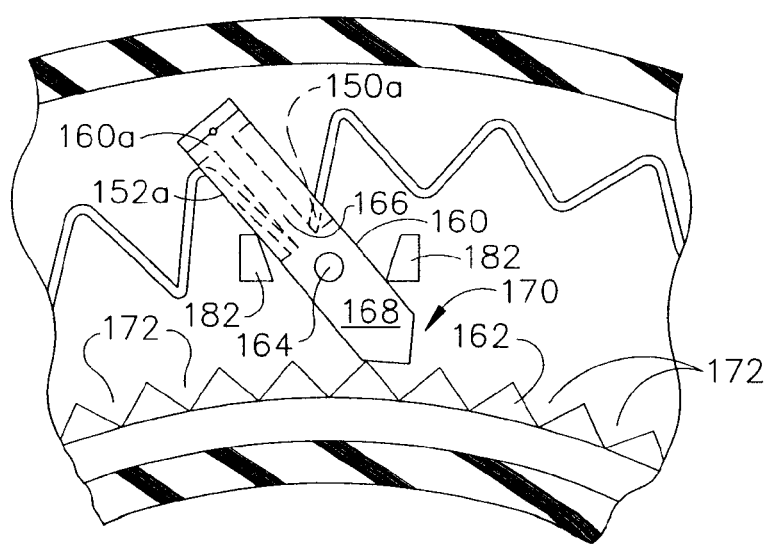
FIG. 5 is an enlarged, fragmentary side view of the ratchet and pawl of the band of FIG. 2.

To adjust the size of area 180, and thusly the stoma size, either actuator 150 or 152 is actuated. In the embodiment depicted, to reduce the size of area 180, actuator 150 is actuated, as seen in FIG. 4. As seen in FIGS. 4 and 5, when actuator 150 is actuated, shroud 178 restrains outward movement of actuator 150, resulting in end 150a urging against upper portion 166, rotating pawl 160 counter clockwise and disengaging angle 170 from notches 172. Stops 182 prevent excessive rotation of pawl 160 in either direction, while allowing sufficient rotation for pawl 160 to disengage ratchet 162. As actuator 150 extends in length, and pawl 160 disengages ratchet 162, first and second portions 148a and 148b may move relative to each other.

Second end 150b of actuator 150 is connected to distal end 148b' of second portion 148b. Upon disengagement of pawl 162, actuator 150 urges distal end 148b' clockwise in FIG. 5 and first portion 148a, via the force exerted on pawl 160 through pivot 164 to shroud 178, counterclockwise, increasing the amount of overlap between first portion 148a and second portion 148b, reducing the size of area 180. When the desired size of area 180 is reached, element 154 is deactivated, and when the pressure of the medium within actuator 150 drops sufficiently, pawl 160 reengages ratchet 162, thereby maintaining the desired size of area 180.

In positions where one actuator is compressed and the other actuator is extended, such as seen in FIG. 4, springs 174 and 176 are sufficient to overcome any moment on pawl 160 created by unactuated actuators 150 and 152, and maintain pawl 160 in engagement with ratchet 162.

Self contained actuators 150 and 152 are not limited to use with the configuration of band 148, nor is band 148 limited to use with self contained actuators. Suitable variations will be apparent to those of ordinary skill in the art.

Figure 2:
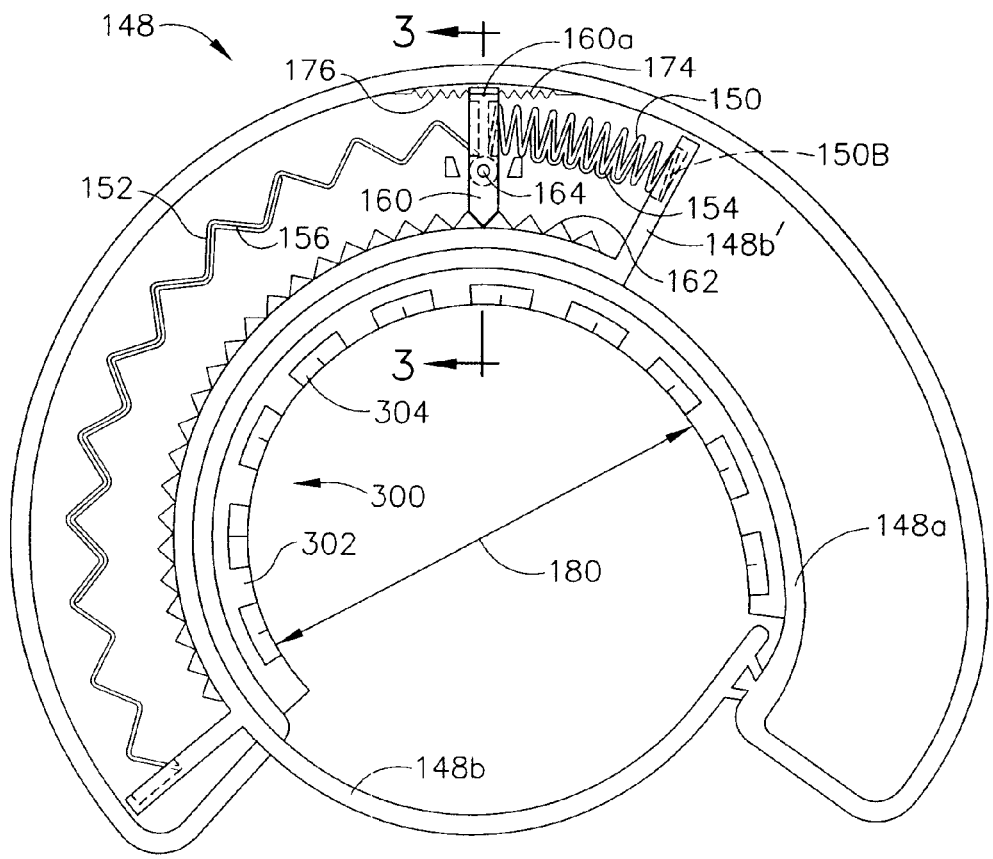
FIG. 2 is a plan view of an exemplary gastric band with a pressure sensing strip.
Figure 3:
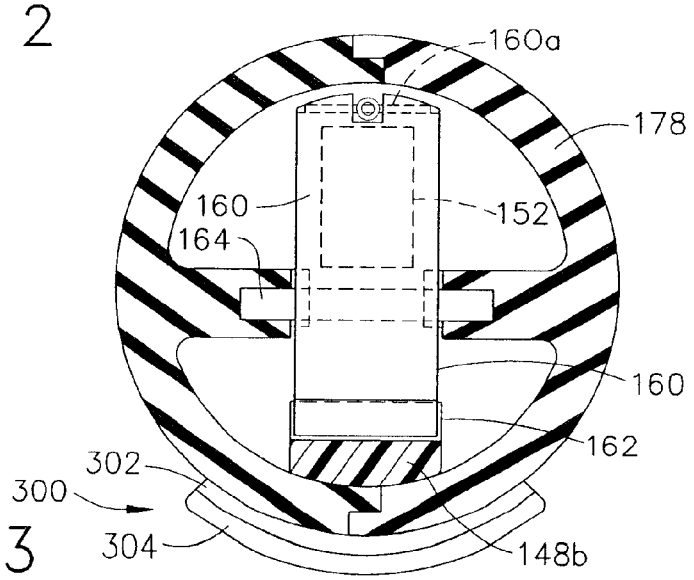
FIG. 3 is a side view in cross section taken along line 3-3 of FIG. 2.

Adjustable band 148 of the present example further comprises a pressure sensing strip 300. Pressure sensing strip 300 comprises a flexible substrate 302 having a plurality of pressure sensing elements 304 disposed therein or thereon. Pressure sensing strip 300 is secured to first portion 148a, such as by an adhesive or by any other suitable means. Each of the pressure sensing elements 304 is operable to sense pressure, such as by converting a physical deflection into an electrical signal, and thereby provide pressure data. Pressure sensing elements 304 may comprise any suitable type(s) of pressure sensors, including but not limited to piezoresistive, capacitive, strain gauges, or any other suitable sensor type, including combinations thereof. Each of the pressure sensing elements 304 is in communication with a wire or other type of communication conduit, which is operable to transmit data indicative of pressure sensed by pressure sensing elements 304. While ten pressure sensing elements 304 are shown in FIGS. 2 and 4, it will be appreciated that any suitable number of pressure sensing elements 304 may be used in any suitable arrangement. For instance, pressure sensing elements 304 may be arranged in a generally straight line or arrayed in some other pattern.

In the present example, pressure sensing strip 300 is configured to fit between a gastric band 148 and a patient's stomach 16. Pressure sensing strip 300 may thus be used to sense pressure at the tissue interface of the stomach 16 and gastric band 148. Pressure sensing strip 300 may be used to determine an average pressure at such interface and/or may be used to obtain a plurality of discrete pressure measurements at multiple points around such interface. Pressure sensing strip 300 may be oriented such that pressure sensing elements 304 face stomach 16 or gastric band 148. Alternatively, pressure sensing elements 304 may be provided on both sides of pressure sensing strip 300. In yet another embodiment, a plurality of pressure sensing elements 304 are integrated directly into first portion 148a. For instance, pressure sensing elements 304 may comprise a MEMS pressure or stress sensor array from Lawrence Livermore National Laboratory. Other suitable types of pressure sensing elements 304 and locations for pressure sensing elements 304 will be apparent to those of ordinary skill in the art.

In view of the foregoing, it will be appreciated that pressure sensing elements 304 may be used to obtain discrete pressure measurements around tissue adjacent to such pressure sensing elements 304. Pressure sensing elements 304 may be configured such that each pressure measurement may be associated with a particular pressure sensing element 304, which may permit association of pressure measurements with particular tissue locations. For instance, being able to associate pressure measurements with particular tissue locations may permit a user to determine whether there is too much or too little pressure against a particular tissue location. Similarly, discrete pressure measurements may be used to identify points of tissue erosion, to detect migration of gastric band 38, or for other purposes.

Furthermore, to the extent that discrete pressure measurements may be obtained using a plurality of pressure sensing elements 304, a pressure profile may be generated. For instance, a pressure profile may correlate a given pressure measurement with a particular sensor, and therefore with a particular location on a gastric band 148 and/or stomach 16. Similarly, a pressure profile may be used to establish how pressure is allocated along the length or circumference of the interface of a gastric band 148 and stomach 16. It will also be appreciated that discrete pressure measurements and/or a pressure profile may be geometrically reconstructed to show the relative shape and/or size of food being swallowed by a patient, or for other purposes. Other ways in which a pressure profile may be established and/or used will be apparent to those of ordinary skill in the art.

Suitable structures or techniques for correlating a pressure measurement with a particular pressure sensing element 304 will be apparent to those of ordinary skill in the art. In one embodiment, each pressure sensing element 304 has an associated identification code, which may be transmitted with pressure data obtained with the corresponding pressure sensing element 304. Alternatively, each pressure sensing element 304 may be associated with a dedicated data interface port (not shown), and each such port may transmit or otherwise be associated with a unique identification code. In another variation, as discussed in greater detail below, each pressure sensing element 304 may be configured to provide a unique reflected signal or signature that distinguishes each sensing element 304 from other sensing elements 304.

As another variation, pressure measurements may be averaged, compared, or otherwise combined by a local component (e.g., an ASIC, etc.) on a pressure sensing strip 300, such that a pressure value communicated externally is not associated with a particular pressure sensing element 304. Of course, some other component (e.g., an external component, etc.) may also average, compare, or otherwise combine pressure measurements. Other ways in which discrete or averaged pressure measurements may be obtained, communicated, handled, and used will be apparent to those of ordinary skill in the art.

In one embodiment, pressure data is communicated from pressure sensing elements 304 via a wire (not shown) to a transmitter (not shown). The transmitter is operable to further communicate the pressure data wirelessly to a receiver external to the patient. For instance, the transmitter may comprise one or more RF coils operable to provide telemetry with receiver coils located external to the patient. Similarly, to the extent that pressure sensing elements 304 require power from an external source for operation, the RF coils used to provide telemetry may also be used to provide transcutaneous energy transfer (TET). Alternatively, a dedicated set of TET coils may be provided. In another embodiment, a battery or other internal power source is provided in the transmitter, pressure sensing strip 300, or elsewhere. In any event, a transmitter, TET coils, a battery, and/or any other component in communication with a wire may be positioned in any suitable location.

In yet another embodiment, a coil (not shown) is provided within pressure sensing strip 300. Each pressure sensing element 304 is in communication with the coil. As with the telemetry and TET coils discussed above, the coil may be operable to provide both telemetry and TET with an external device. Alternatively, separate coils within pressure sensing strip 300 may be used—one for telemetry and one for TET. In yet another embodiment, one or more coils are provided within pressure sensing strip 300 while one or more other coils are provided elsewhere. In yet another embodiment, each pressure sensing element 304 has a respective discrete coil (not shown) that is operable to provide telemetry and/or TET.

It will be appreciated that pressure sensing elements 304 may be un-powered or passive. For instance, a pressure sensing element 304 may be configured to reflect a signal transmitted from an external transmitter such as a telemetry coil. The reflected signal may then be read and demodulated or decoded by the transmitter device or by some other receiver. The reflected signal may indicate a parameter (e.g., pressure, etc.) sensed by a sensor. By way of example only, each pressure sensing element 304 may comprise a sensor such as any of the sensors described in U.S. Pat. No. 6,855,115, issued Feb. 15, 2005, and entitled "Implantable Wireless Sensor for Pressure Measurement within the Heart;" U.S. Pub. No. 2003/0136417, published Jul. 24, 2003, and entitled "Implantable Wireless Sensor;" and/or WO 03/061504, published Jul. 31, 2003, and entitled "Implantable Wireless Sensor." The disclosure of each of U.S. Pat. No. 6,855,115; U.S. Pub. No. 2003/0136417; and WO 03/061504 is incorporated by reference herein. Of course, any of the transmitters or receivers described in those references may also be used. Furthermore, any sensor or sensing element described herein may be provided as an un-powered or passive element. It will also be appreciated that each sensor may be configured to provide a unique reflected signal or signature that distinguishes each sensor from other sensors. Such unique signals or signatures may permit a pressure profile to be generated. Other ways of providing a wireless, passive, and/or reflective sensor will be apparent to those of ordinary skill in the art.

In still another embodiment, one or more of pressure sensing elements 304 are in communication with an implanted controller (not shown), which also selectively applies electrical signals to element 154 and element 156 as described above. In this embodiment, signals indicative of pressure from pressure sensing elements 304 are processed by the controller to influence the electrical signals applied to element 154 and element 156 by the controller. For instance, the controller may be preprogrammed with a maximum or ideal pressure level, and the controller may apply electrical signals to element 154 and element 156 while receiving feedback pressure signals from pressure sensing elements 304 until the maximum or ideal pressure level is reached. The controller may then cease applying electrical signals to element 154 and element 156. Of course, signals from pressure sensing elements 304 may be used as feedback or otherwise in any other suitable way.

Still other variations of pressure sensing strip 300 will be apparent to those of ordinary skill in the art. By way of example only, pressure sensing strip 300 may be substituted by, supplemented with, or varied in accordance with any of the pressure sensing devices disclosed in U.S. Non-Provisional application Ser. No. 11/682,459, filed Mar. 6, 2007, entitled "Pressure Sensors for Gastric Band and Adjacent Tissue," the disclosure of which is incorporated by reference herein. Similarly, any gastric band described herein or in any of the applications/publications that have been incorporated by reference herein may be modified with any suitable version of pressure sensing strip 300 or pressure sensing elements 304 without pressure sensing strip 300.

Figure 6:
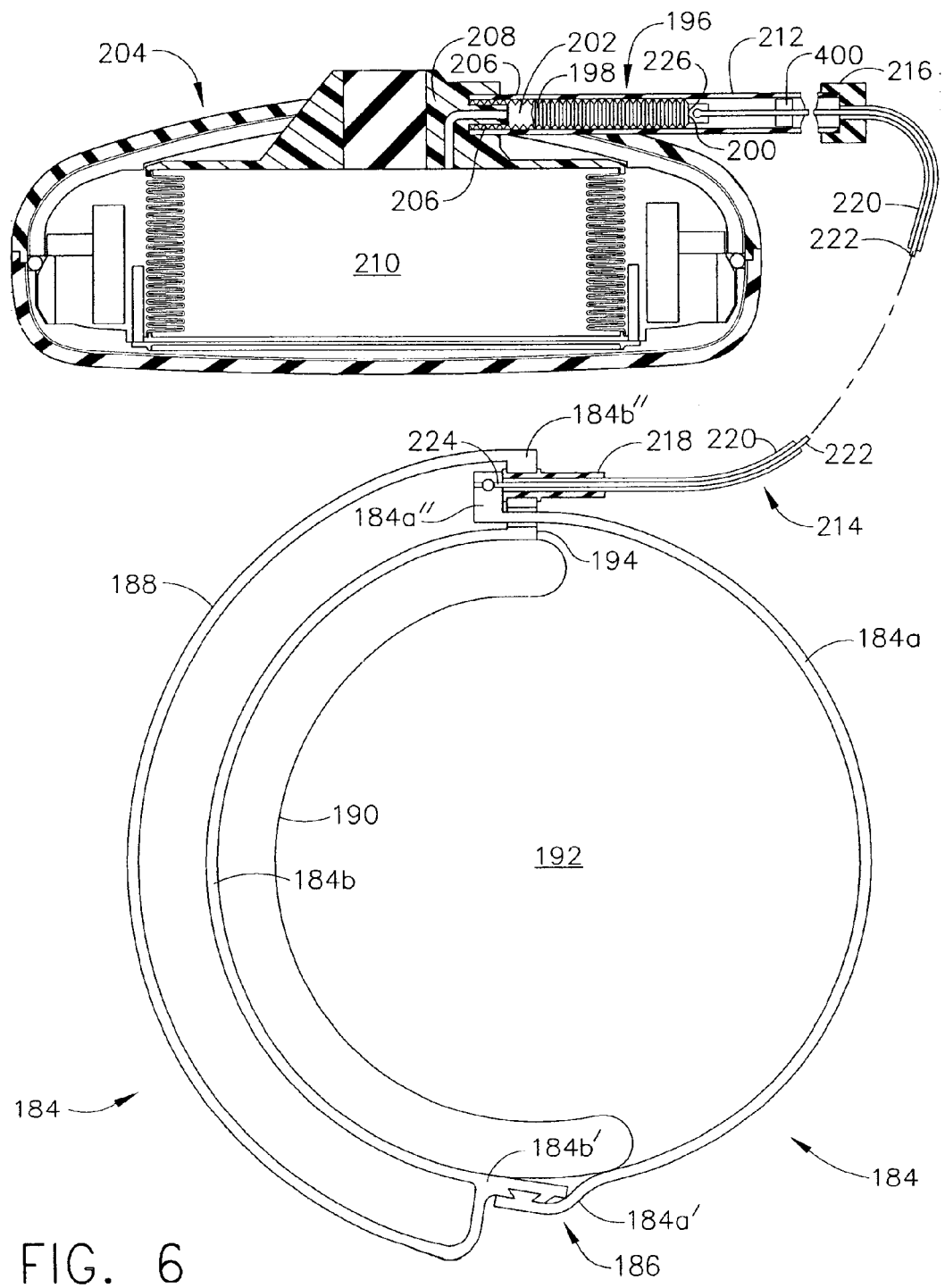
FIG. 6 is a plan view of another exemplary embodiment of a gastric band, with a force sensor in an actuating mechanism.

FIG. 6 illustrates another embodiment of an actuator, in conjunction with another embodiment of an adjustable band 184. Band 184 includes first portion 184a and second portion 184b, with each portion having attachment mechanism 186 which may be used to connect ends 184a' and 184b' together after band 184 has been disposed about an anatomical feature. Although attachment mechanism 186 is depicted as having a transverse dove tail configuration, any attachment mechanism may be used. Second portion 184b includes a shroud 188 which encloses end 184a" throughout its travel, as described below.

Band 184 is comprised of any suitable biocompatible material having sufficient resilience, strength, and fatigue resistance, such as implant grade silicone. Of course, any other material(s) having any suitable properties may be used. The inner surface may be of any suitable configuration which does irritate or damage adjacent tissue, such as for example, as shown in U.S. Provisional Patent Application Ser. No. 60/530,497, filed Dec. 17, 2003, for Mechanically Adjustable Gastric Band, which is incorporated by reference. Second portion 184b may have a balloon 190 disposed on its inner surface, which is depicted as extending past attachment mechanism 186. Balloon 190 may have a fixed volume. It is noted that, in the embodiment depicted, the inner surface of first portion 184a does not have a similar feature, though it may in alternative embodiments. As illustrated in FIG. 6, band 184 is at its largest size, encircling area 192, having a diameter of approximately 1.35 inches (34.29 mm), for example only. At its smallest size, when end 184a" has traveled its full distance within shroud 188, most of first portion 184a is disposed within shroud 188, the ends of balloon 190 are proximal each other and area 192 has a diameter of about 0.71 inches (18 mm) by way of example only. (It is noted that although area 192 is depicted as generally circular and is referred to as having a diameter, area 192 is not limited to a circle or circular shape.) Thus, in the embodiment depicted, first portion 184a is small enough to move through opening 194, and the inner surface of first portion 184a does not have any features, such as a balloon, which would interfere with such movement. Of course, these components may be arranged and configured in a number of alternative ways.

Actuator 196 is depicted as comprising generally cylindrical bellows 198, which is illustrated as a corrugated member having a series of folds creating spaced apart circular ridges. Although the ridges and folds are illustrated as being parallel, and evenly shaped and spaced, they are not required to be. Bellows 198 may be made from any suitable biocompatible material, such as titanium which is MRI safe. Bellows 198 is closed at end 200, defining internal cavity 202. Internal cavity 202 may be in fluid communication with a source of fluid, which may be a remotely operated bidirectional infuser 204, similar to infuser 64, or any other fluid source capable of repetitively bidirectionally moving fluid. In the embodiment depicted, end 206 of bellows 198 is secured to housing 208 of bidirectional infuser 204, placing internal cavity 202 in fluid communication with variable internal volume 210. In the embodiment depicted, the fluid within internal cavity 202 and internal volume 210 may be saline solution or any other fluid. Movement of bellows 198 is constrained to be longitudinal by bellows housing 212, which is secured to housing 208.

Drive cable assembly 214 is provided between bellows housing 212 and band 184. Cable drive assembly 214 includes fitting 216, which is secured to bellows housing 212, and fitting 218, which is secured to end 184b", each being secured in any suitable manner. Sheath 220 extends between fittings 216 and 218, providing a mechanical ground for cable 222 disposed therein. Cable end 224 is secured to end 184a", and cable end 226 is secured to bellows end 200, each being secured in any suitable manner.

To actuate actuator 196, fluid from internal volume 210 is forced through fluid port 228, lengthening bellows 198. As a result of the relative cross sectional areas of bellows 198 and internal volume 210, bellows 198 acts as an amplifier, with a small amount of fluid producing the longitudinal expansion required to adjust the size of band 184. As end 200 moves within bellows housing 212, cable end 224 moves band end 184a" within shroud 188 relative to portion 184b, thereby decreasing the size of the stoma created by band 184. To increase the size of the stoma, fluid is withdrawn from bellows 198, retracting cable 222, moving end 184a" toward end 184b".

Cable assembly 214 may be made of any suitable biocompatible material. Cable end 224 of this example is sufficiently stiff to push end 184a" within shroud 188 the desired distance. Shroud 188 protects surrounding tissue from the movement of end 184a", and also constrains the movement of cable end 224 and cable 222, functioning similarly to sheath 220, to produce the desired movement of end 184a".

In the present example depicted in FIG. 6, a force sensor 400 is engaged with cable 222. Force sensor 400 is operable to sense force exerted on or by cable 222. Force sensor 400 may comprise any suitable type of force sensor, including but not limited to a mechanical, hydraulic, strain gauge, piezoresistive, or piezoelectric type of force sensor. By way of example only, one side of force sensor 400 may be coupled with bellows end 200 and/or a segment of cable 222, with the other side of force sensor 400 being coupled with another segment of cable 222. In other words, cable 222 may be provided in two segments, with a first segment being provided on one side of force sensor 400 and second segment being provided on the other side of force sensor 400. Coupling of force sensor 400 with cable 222 or any other component may be provided by a linkage or any other suitable structure or technique. Other suitable configurations and techniques for engaging force sensor 400 with cable 222 will be apparent to those of ordinary skill in the art. Similarly, other suitable locations for force sensor 400 will be apparent to those of ordinary skill in the art. It will also be appreciated that force sensor 400 may comprise a diaphragm, a strain element, a resilient member, or any other suitable component(s) configured to sense force.

Force sensed by force sensor 400 may be indicative of or correlated with pressure exerted by gastric band 184 on a patient's stomach 16. In addition, similar to pressure sensing elements 304 discussed above, force sensor 400 may communicate a signal indicative of force to an implanted controller (e.g., via wire), to a receiver located external to the patient (e.g., via RF telemetry), and/or to any other suitable location. Signals indicative of force from force sensor 400 may also be used in a manner similar to those described above with respect to signals indicative of pressure from pressure sensors 304. It will also be appreciated that any gastric band described herein or in any of the applications/publications that have been incorporated by reference herein may be modified with any suitable version of force sensor 400.

Figure 7:
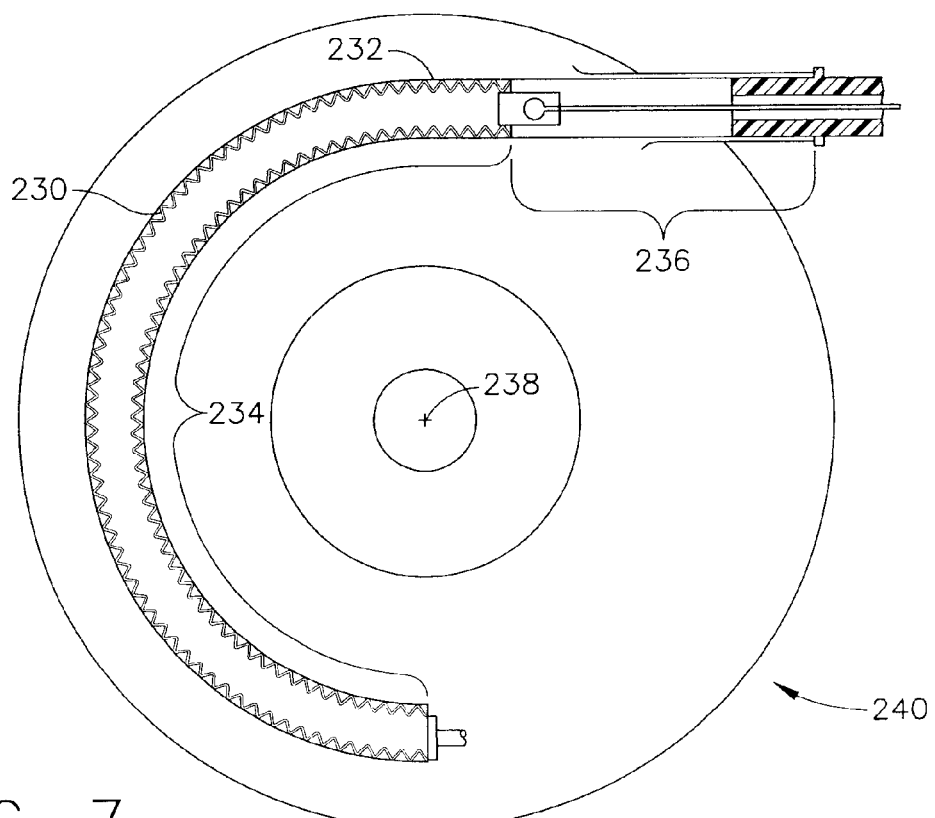
FIG. 7 is a top view of an exemplary embodiment of a bidirectional infuser.
Figure 8:
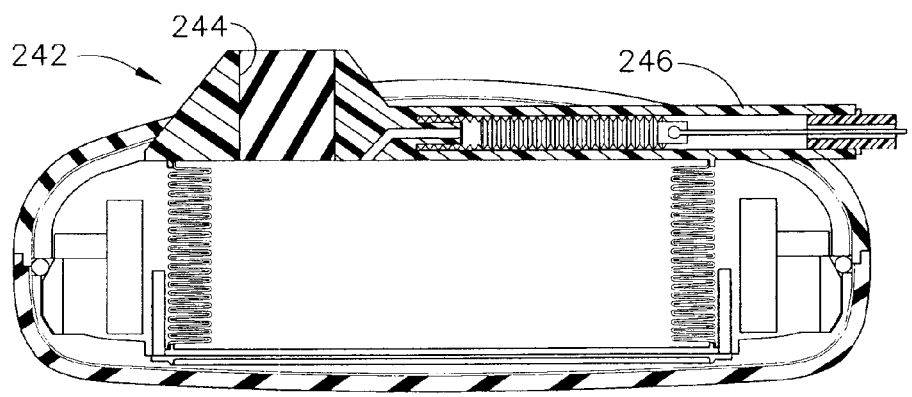
FIG. 8 is a side view in partial cross section of another exemplary embodiment of a bidirectional infuser.
Figure 9:
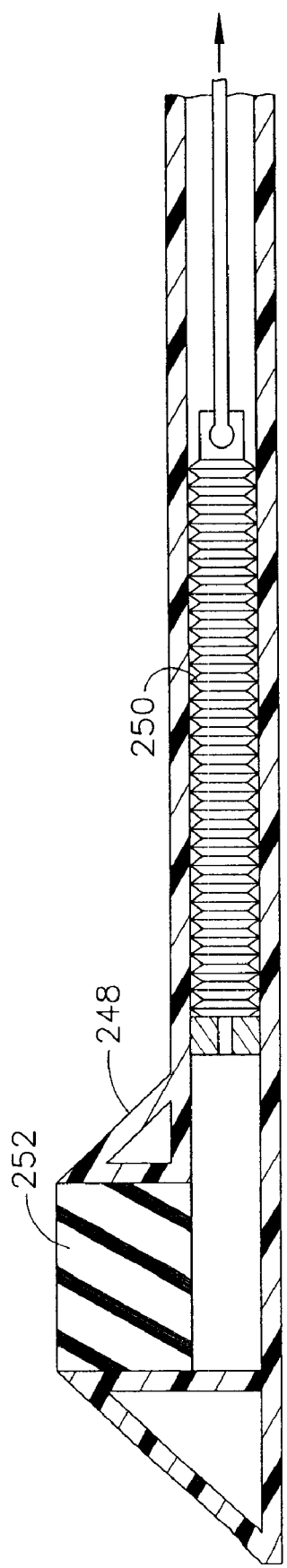
FIG. 9 is a side view of an exemplary injection port.

FIGS. 7-9 illustrate alternate embodiments of bidirectional infusers showing alternate configurations of a bellows. FIG. 7 illustrates bellows 230 disposed within bellows housing 232 having arcuate portion 234. Bellows housing 232 may include straight section 236 as shown. The arcuate configuration allows the length of bellows housing 232 to be longer than the distance from center 238 while not extending very far beyond the circumference of bidirectional infuser 240, increasing the available stroke of bellows 230. Bellows housing 232 may be secured to infuser 240 in any suitable manner, or may be formed integrally therewith. FIG. 8 illustrates bidirectional infuser 242 with septum 244 offset from the center of outer periphery of infuser 242. This allows the portion of bellows housing 246 overlying infuser 242 to be longer in comparison to bidirectional infuser 204 which has a centrally disposed septum. FIG. 9 illustrates injection port 248 with bellows 250. To actuate bellows 250, fluid is injected or withdrawn via septum 252. It will be appreciated that any of these infusers/ports may be used with any type of band. In other words, any component described herein may be combined or interchanged with any other component described herein, as desired. It will also be appreciated that, in these configurations (among others), a pressure sensor may be incorporated in the fluid path (e.g., within internal volume 210, etc.) to sense a change in fluid pressure when fluid is added, removed or compressed. This may provide a secondary feedback of the adjusted stroke of an actuator 196, which may be translated to the diameter change in an associated gastric band 184.

Figure 10:
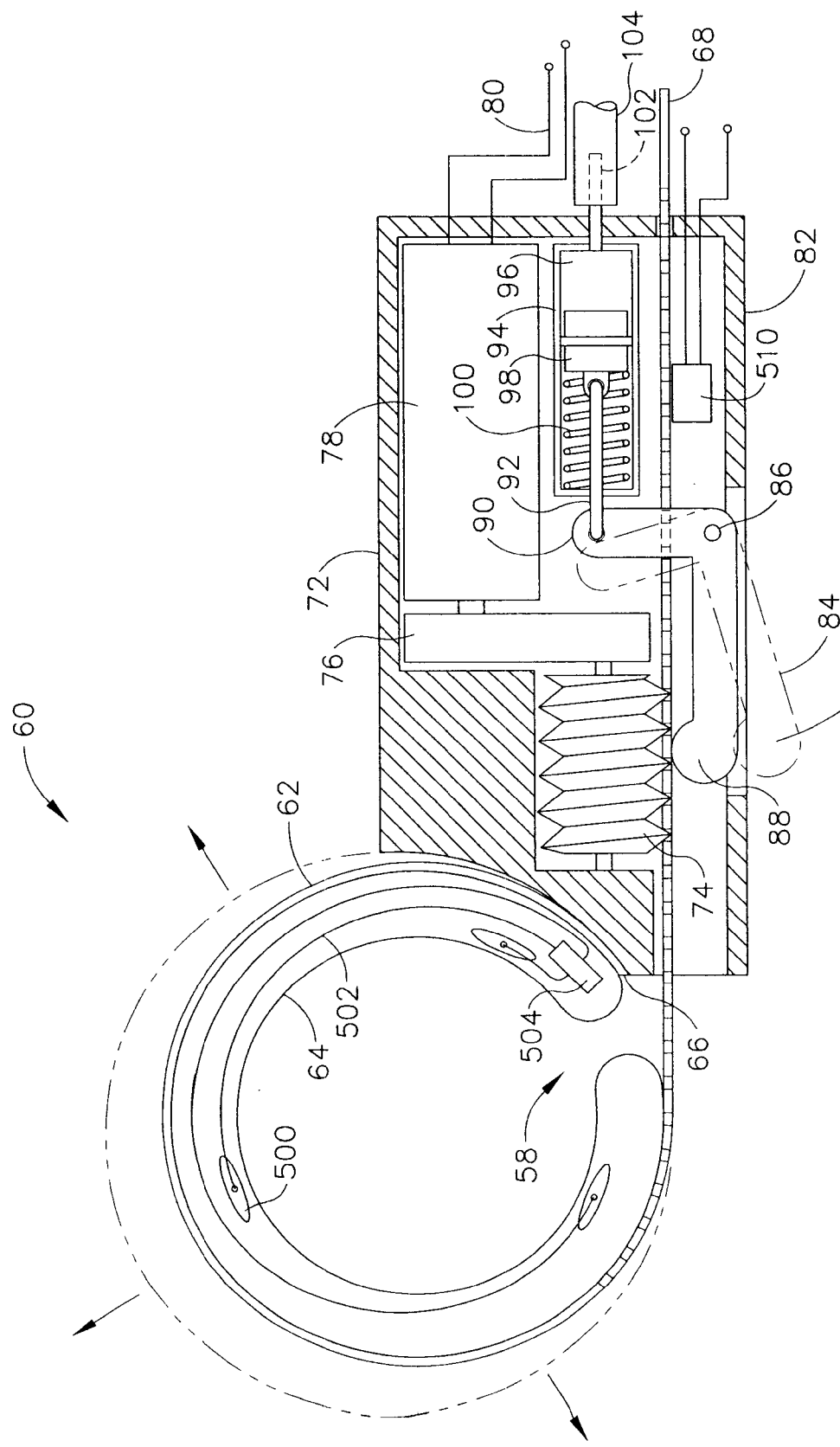
FIG. 10 is a side cross-sectional view of another exemplary gastric band, with proximity sensors and a linear displacement sensor.
Figure 11:
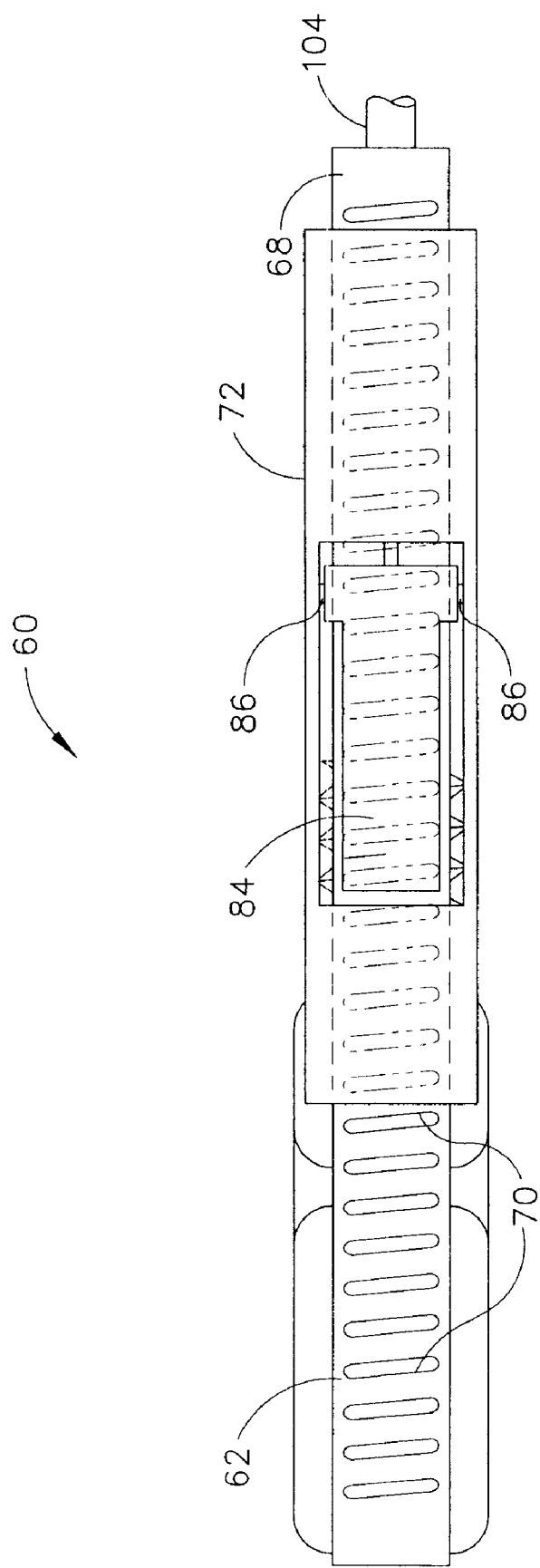
FIG. 11 is a bottom view of the gastric band of FIG. 10.

FIGS. 10-11 depict yet another exemplary gastric band 60. Versions of gastric band 60, as well as other implantable restriction devices, are disclosed in European Patent Application Publication EP1547549A2, published Jun. 29, 2005, entitled "Mechanically Adjustable Gastric Band," the disclosure of which is incorporated by reference herein. Gastric band 60 of the present example comprises a band 62 that has a first end 66 and a second end 68 and forms an enclosure 58 to restrict food intake through the stomach of a patient. Band 62 is made of a spring-like, non-magnetic (for MRI compatibility) material and is in a straight configuration when in a unconstrained mode. A cushion 64 is made of a soft, biocompatible material such as silicone and attaches to the inside of band 62 to interface with the stomach tissue. Other suitable materials and configurations for band 62 and cushion 64 will be apparent to those of ordinary skill in the art.

Figure 12:
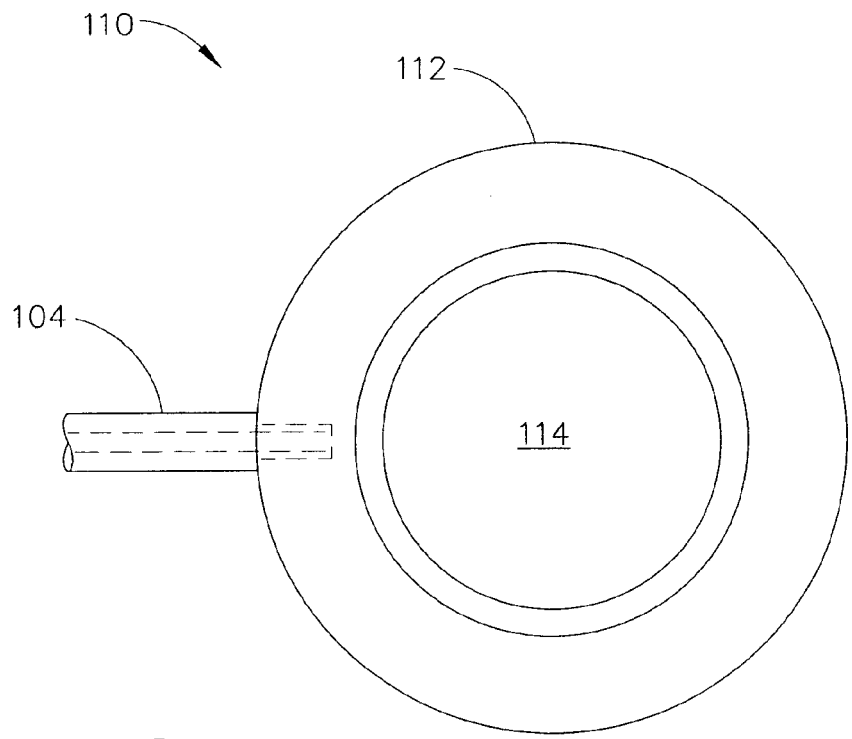
FIG. 12 is a plan view of an exemplary injection port that may be used with the gastric band of FIG. 10.
Figure 13:
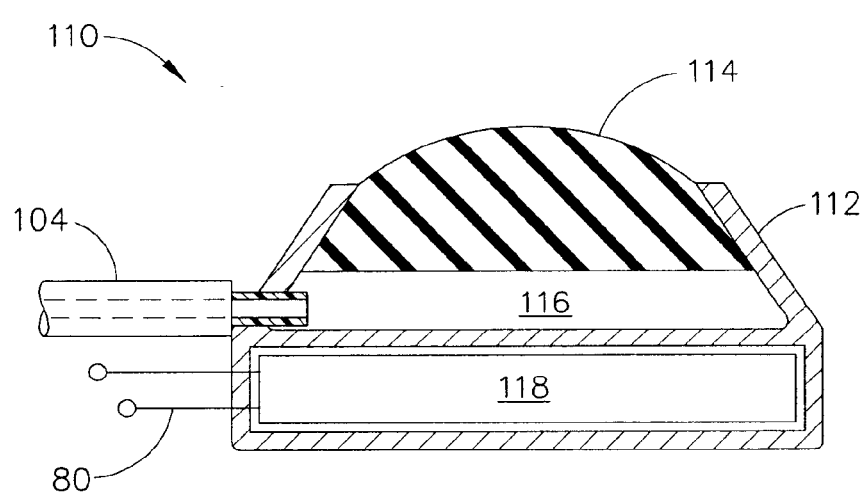
FIG. 13 is a side cross-sectional view of the injection port of FIG. 12.

First end 66 of band 62 attaches to a band actuator 72. Second end 68 of band 62 inserts into band actuator 72 after the surgeon has placed band 62 around the stomach. Band actuator 72 comprises a motor 78, which drives a pinion 74 through a transmission 76. Electrical conductors 80 electrically connect motor 78 to an implantable control port 110, which is shown in FIGS. 12-13, having a control unit 118. Pinion 74 operationally engages a plurality of slots 70 of band 62. When motor 78 rotates in a first direction, enclosure 58 reduces in diameter; when motor 78 rotates in an opposite second direction, enclosure 58 increases in diameter. The surgeon may therefore control the amount of restriction to food intake through the stomach.

FIGS. 10-11 also show a release mechanism 94 inside of band actuator 72. Release mechanism 94 comprises a lever 84 having an axle 86, a first end 88, and a second end 90. When in an engaging mode, first end 88 bears against band 62, thus maintaining operational engagement of band 62 with pinion 74. When in a releasing mode, first end 88 is swung away about axle 86 from band 62, thus allowing band 62 to be disengaged from pinion 74. Release mechanism 94 further comprises a piston 98 that attaches via a link 92 to second end 90 of lever 84. A spring 100 normally urges piston 98 to move in a direction that causes lever 84 to be in the engaging mode. A chamber 96 containing piston 98 fluidly attaches to a tube 104 via a fitting 102. Tube 104 fluidly connects to a reservoir 116 formed within a housing 112 of implantable control port 110, shown in FIGS. 12-13. Implantable control port 110 further includes a septum 114 made of silicone and which is needle penetrable so that a surgeon may inject a fluid into reservoir 116 and actuate piston 98 of release mechanism 94. Implantable control port 110 may be implanted subcutaneously in a patient to be within the transcutaneous energy transmission range, and to allow the surgeon to access septum 114 to inject a fluid into reservoir 116. Release mechanism 94 allows non-surgical release of the constriction of band 62 on the stomach in the event of electromechanical failure.

Release mechanism 94 is not limited to hydraulic actuation as described above, but may instead incorporate a pneumatic, electrical, or any other type of actuation. Implantable control port 110 may therefore be modified to omit septum 114, reservoir 116, and tube 104. Furthermore, control unit 118 may be integrated into gastric band 60 or otherwise provided. It will also be appreciated that release mechanism 94 or modified versions thereof may be used with gastric bands that are actuated with devices other than electric motors. For example, release mechanism 94 may be used with a gastric band that is inflatable with a fluid such as saline. In other embodiments, release mechanism 94 is omitted altogether. Still other variations of gastric band 60 and its components will be apparent to those of ordinary skill in the art.

In the present example, a plurality of proximity sensors 500 are provided within cushion 64. Each proximity sensor 500 comprises a coil, and proximity sensors 500 are associated with a resonant RF frequency. Of course, any other type of proximity sensor 500 may be used. Each proximity sensor 500 of the present example is in communication with a coil interface circuit 504 via a respective wire 502. Coil interface circuit 504 is configured to sense inductance and/or capacitance change relative to proximity sensors 500. In particular, as band 62 is pulled by pinion 74, thereby effectively shrinking the inner diameter defined by cushion 64, proximity sensors 500 are drawn closer together. Such relative movement of proximity sensors 500 causes a change in the resonant frequency associated with the proximity sensors 500, as the resonant frequency changes with respect to the capacitance and/or inductance change occurring when proximity sensors 500 are moved relative one another. The change in the inner diameter defined by cushion 64 may therefore be determined by the change in resonant frequency, capacitance, and/or inductance encountered upon corresponding movement of proximity sensors 500. Coil interface circuit 504 may therefore sense the proximity of proximity sensors 500 relative one another. Alternatively, proximity sensors 500 and coil interface circuit 504 may operate under any other suitable principles.

The change in resonant frequency, capacitance, and/or inductance encountered upon movement of proximity sensors 500 may be communicated to any other component in any suitable fashion. For instance, a signal indicative of resonant frequency, capacitance, and/or inductance change may be communicated by coil interface circuit 504 to control unit 118 to influence the rotation of pinion 74 by motor 78. In particular, signals from coil interface circuit 504 may be used as feedback to prevent overtightening of gastric band 60. Alternatively, signals from coil interface circuit 504 may be communicated to a device (not shown) that is located external to the patient. Coil interface circuit 504 may also receive power from any suitable internal (e.g. a battery) or external power source (e.g., via TET). Accordingly, it will be appreciated that proximity sensors 500 and coil interface circuit 504 may be used in any manner similar to those described above with respect to pressure sensing elements 304 and force sensor 400. Other variations will be apparent to those of ordinary skill in the art. It will also be appreciated that any gastric band described herein or in any of the applications/publications that have been incorporated by reference herein may be modified with any suitable version of proximity sensors 500.

As is also shown in FIG. 10, a gastric band 60 may comprise a linear displacement sensor 510. In the present example, linear displacement sensor 510 comprises a linear voltage displacement transducer, though any other type of linear displacement sensor may be used. While shown on a band 60 that has proximity sensors 500, it will be appreciated that linear displacement sensor 510 may be provided on any other band, including but not limited to a band that lacks any other type of sensor. In this example, linear displacement sensor 510 is engaged with band 62. Other suitable locations for linear displacement sensor 510 will be apparent to those of ordinary skill in the art.

Linear displacement sensor 510 of the present example is able to determine linear displacement of band 62 relative to the housing of band actuator 72 by sensing the linear displacement of linear displacement sensor 510 relative to a reference position. For instance, the position of linear displacement sensor 510 may be established or "zeroed out" prior to an adjustment of band 62, and as band 62 is tightened, linear displacement sensor 510 may sense its displacement from such a reference position. In another embodiment, linear displacement sensor 510 comprises an arm or other component (not shown) that is secured to the housing of band actuator 72. Such an arm or other component may move within the linear displacement sensor 510, and the displacement of the arm or other component within linear displacement sensor 510 may constitute the displacement sensed by linear displacement sensor 510. Alternatively, any other components or principles of operation for a linear displacement sensor 510 may be incorporated.

It will be appreciated that the linear displacement sensed by linear displacement sensor 510 of the present example may be indicative of or correlated with the effective inner diameter defined by cushion 64. Linear displacement sensor 510 may communicate signals indicative of linear displacement in any suitable fashion. For instance, linear displacement sensor 510 may communicate linear displacement signals to control unit 118 to influence the rotation of pinion 74 by motor 78. Alternatively, signals from linear displacement sensor 510 may be communicated to a device (not shown) that is located external to the patient. Accordingly, it will be appreciated that linear displacement sensor 510 may be used in any manner similar to those described above with respect to pressure sensing elements 304, force sensor 400, and/or proximity sensors 500. Other variations will be apparent to those of ordinary skill in the art. It will also be appreciated that any gastric band described herein or in any of the applications/publications that have been incorporated by reference herein may be modified with any suitable version of linear displacement sensor 510.

In another embodiment the current supplied by motor 78 is sensed via electrical conductors 80 and control unit 118. As with other sensed parameters described herein, the sensed current may be processed by a device that is external to the patient or may be processed by a device that is within the patient (e.g., within control unit 118). In any case, the amount of current supplied by motor 78 may be indicative of torque provided by motor 78, such that sensed current may be translated into sensed torque. It will be appreciated that some assumptions may need to be made in order to correlate current with torque, such as an assumption that the voltage is fixed. It will also be appreciated that torque may be sensed using a torque sensor (not shown) or using any other suitable device or processing.

Regardless of how obtained, sensed torque may be provided in a feedback loop to regulate control of motor 78, to an external device for monitoring purposes, or to any other component or device for any other purpose. Accordingly, it will be appreciated sensed torque may be used in any manner similar to sensed parameters described above with respect to pressure sensing elements 304, force sensor 400, proximity sensors 500, and/or linear displacement sensor 510. Other variations will be apparent to those of ordinary skill in the art. It will also be appreciated that any gastric band described herein or in any of the applications/publications that have been incorporated by reference herein may be modified with any suitable implementation of torque sensing.

Figure 14:
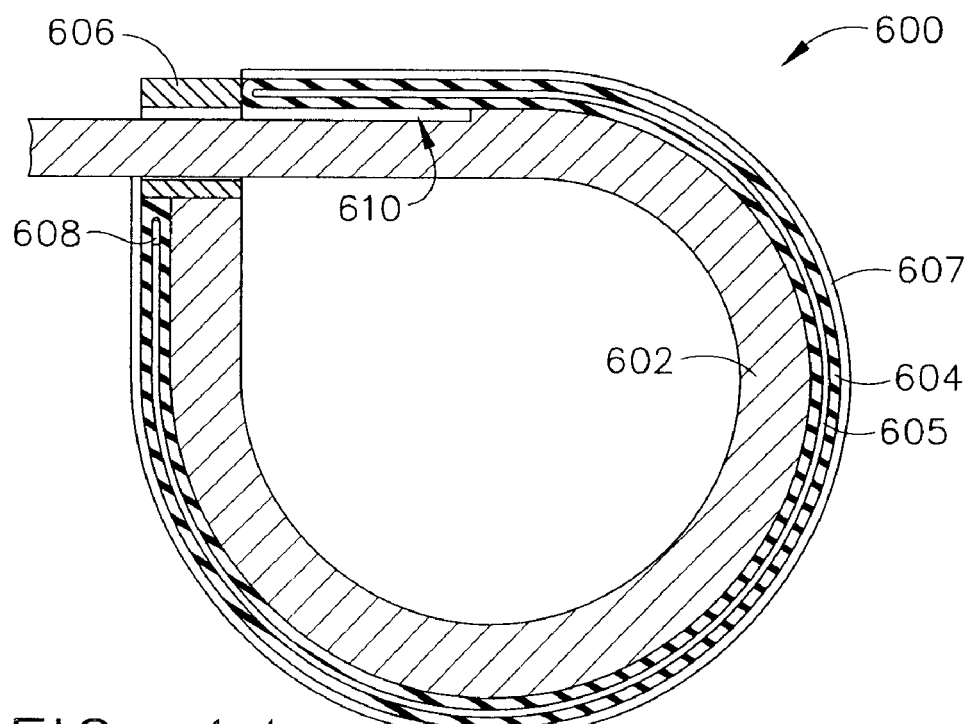
FIG. 14 is a partial, cross-sectional side view of another exemplary gastric band, with a pressure sensor.

FIG. 14 shows another exemplary gastric band 600. In this embodiment, gastric band 600 comprises a flexible yet non-tensile band 602 and a tensile bladder 604 secured to band 602. A rigid strap 607 is secured to the outer side of bladder 604. By way of example only, band 602 may comprise a metal, plastic, textile, or any other material(s), including combinations thereof. Bladder 604 may comprise silicon or any other suitable material(s), including combinations thereof. Strap 607 may comprise a metal, plastic, or any other suitable material(s), including combinations thereof. Band 602, bladder 604, and strap 607 may have any suitable alternative properties.

One end of band 602 is fixedly secured to a latch 606, while the other end of band 602 is passed through latch 606 and may be adjusted relative to latch 606 to obtain a desired inner diameter defined by band 602. Latch 606 is configured such that, when band 602 is adjusted to provide a desired inner diameter, latch 606 may be manipulated to secure the position of band 602 relative to latch 606. Suitable mechanisms or features for providing such securing by latch 606 will be apparent to those of ordinary skill in the art. Similarly, suitable mechanisms or features for adjusting the position of the free end of band 602 relative to latch 606 will be apparent to those of ordinary skill in the art. By way of example only, the adjustment of band 602 relative to latch 606 may be provided mechanically, hydraulically, by hand, or otherwise.

Each end of bladder 604 is secured to latch 606. Similarly, each end of strap 607 is secured relative to latch 606. By way of example only, one end of bladder 604 may be permanently secured to latch 606, while the other end of bladder 604 may comprise a feature (not shown) that is selectively engageable with latch 606. For instance, such a feature may be used to secure a free end of bladder 604 to latch 606 when gastric band 600 is initially secured to a patient's stomach 16. Bladder 604 defines a vessel 605 holding a fluid (e.g., saline, etc.) and a pressure sensor 608. Pressure sensor 608 is operable to sense the pressure of the fluid within vessel 605. Pressure sensor 608 may be configured to communicate pressure data in a manner similar to communication of data by any other type sensor described herein. For instance, pressure sensor 608 may communicate pressure data to an external device using direct telemetry, using telemetry via an implanted data relay located elsewhere within the patient, or using any other suitable technique. In addition or in the alternative, pressure sensor 608 may communicate data to another implanted device, which may then process the pressure data for any suitable purpose.

Figure 15:
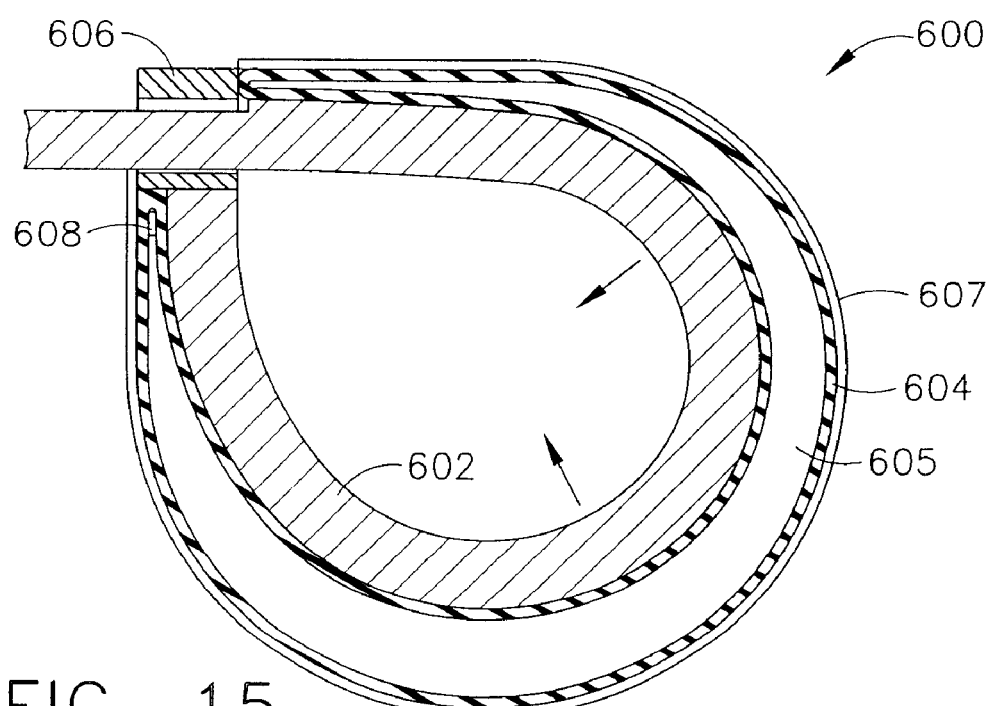
FIG. 15 is a partial, cross-sectional side view of the gastric band of FIG. 14 in an adjusted configuration.

FIG. 14 shows band 602 in an extended configuration, providing a relatively large inner diameter. While a substantial portion of bladder 604 is secured to band 602, such as by an adhesive, etc., a portion of bladder 604 near latch 606 is not secured to band 602, providing a disconnect 610 between band 602 and bladder 604 in the configuration shown in FIG. 14. As shown in FIG. 15, band 602 is pulled further through latch 606 for adjustment to provide a smaller inner diameter, such as to form a restriction in a patient's stomach 16. Disconnect 610 permits band 602 to be pulled further through latch 606 without bladder 604 being pulled through or into latch 606.

As is also shown in FIG. 15, the engagement of bladder 604 with band 602 will cause bladder 604 to stretch or otherwise provide a greater vessel 605 volume when band 602 is pulled further through latch 606. It will be appreciated that, since a fixed amount of fluid is provided in vessel 605, this increase in vessel 605 volume will cause a decrease in the pressure of fluid within vessel 605. Accordingly, the pressure of fluid within vessel 605 will decrease as the inner diameter defined by band 602 decreases. Similarly, if the inner diameter defined by band 602 is increased (e.g., by pushing band 602 back through latch 606), the volume of vessel 605 will decrease, causing an increase in the pressure of fluid within vessel 605. Such changes in pressure may be detected by pressure sensor 608 and communicated as described above. Other variations of gastric band 600, including variations of its components, uses, and principles of operation, will be apparent to those of ordinary skill in the art.

Figure 16:
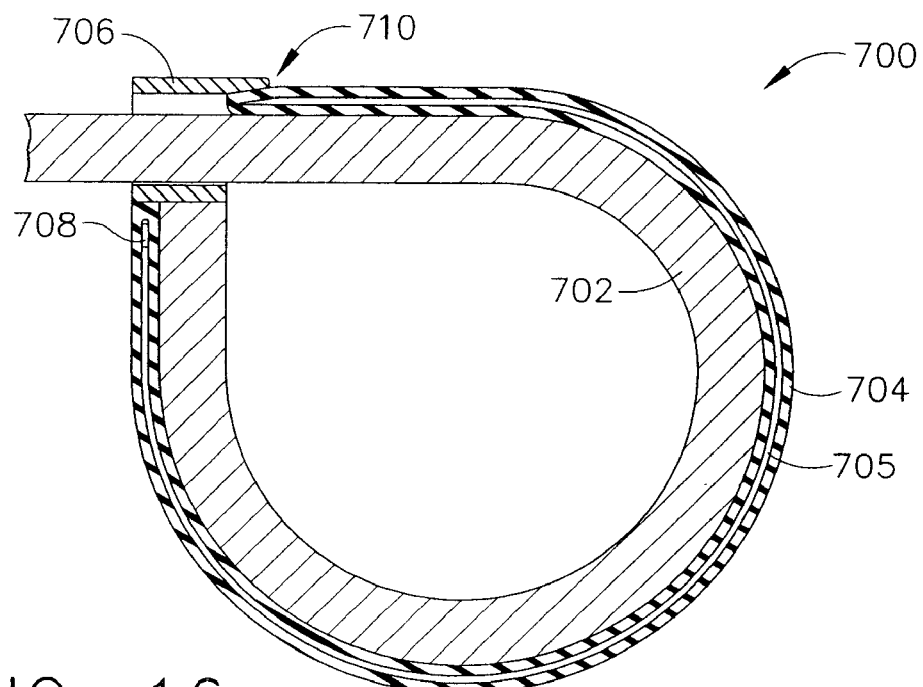
FIG. 16 is a partial, cross-sectional side view of yet another exemplary gastric band, with a pressure sensor.

FIG. 16 shows another exemplary gastric band 700. In this embodiment, gastric band 700 comprises a flexible yet non-tensile band 702 and a flexible yet non-tensile bladder 704 secured to band 702. Suitable materials for band 702 and bladder 704 will be apparent to those of ordinary skill in the art, as will suitable alternative properties of band 702 and bladder 704. In the present example, one end of band 702 is fixedly secured to a latch 706, while the other end of band 702 is passed through latch 706 and may be adjusted relative to latch 706 to obtain a desired inner diameter defined by band 702. Latch 706 is configured such that, when band 702 is adjusted to provide a desired inner diameter, latch 706 may be manipulated to secure the position of band 702 relative to latch 706. Suitable mechanisms or features for providing such securing by latch 706 will be apparent to those of ordinary skill in the art. Similarly, suitable mechanisms or features for adjusting the position of the free end of band 702 relative to latch 706 will be apparent to those of ordinary skill in the art.

Bladder 704 is secured to band 702, such as by an adhesive or other suitable means. In addition, an end of bladder 704 is secured to latch. Bladder 704 defines a vessel 705 holding a fluid (e.g., saline, etc.) and a pressure sensor 708. Pressure sensor 708 is operable to sense the pressure of the fluid within vessel 705. Pressure sensor 708 may be configured to communicate pressure data in a manner similar to communication of data by any other type sensor described herein. For instance, pressure sensor 708 may communicate pressure data to an external device using direct telemetry, using telemetry via an implanted data relay, or using any other suitable technique. In addition or in the alternative, pressure sensor 708 may communicate data to another implanted device, which may then process the pressure data for any suitable purpose.

FIG. 16 shows band 702 in an extended configuration, providing a relatively large inner diameter. Latch 706 of this example comprises a tapered feature 710. As band 702 and bladder 704 are pulled further through latch 706 to provide a smaller inner diameter, such as to form a restriction in a patient's stomach 16, taper feature 710 is configured to squeeze bladder 704. In particular, band 702, bladder 704, and taper feature 710 are configured such that fluid in vessel 705 is forced out of whatever portion of vessel 705 passes taper feature 710 as band 702 and bladder 704 are pulled further through latch 706. In other words, the volume of vessel 705 will decrease as band 702 and bladder 704 are pulled further through latch 706. With a fixed amount of fluid being within vessel 705, it will be appreciated that a decrease in vessel 705 volume will cause an increase in the pressure of the fluid within vessel 705.

Accordingly, the pressure of fluid within vessel 705 will increase as the inner diameter defined by band 702 decreases. Similarly, if the inner diameter defined by band 702 is increased (e.g., by pushing band 702 back through latch 706), the volume of vessel 705 will increase, causing a decrease in the pressure of fluid within vessel 705. Such changes in pressure may be detected by pressure sensor 708 and communicated as described above. Other variations of band 700, including variations of its components, uses, and principles of operation, will be apparent to those of ordinary skill in the art.

Figure 17:
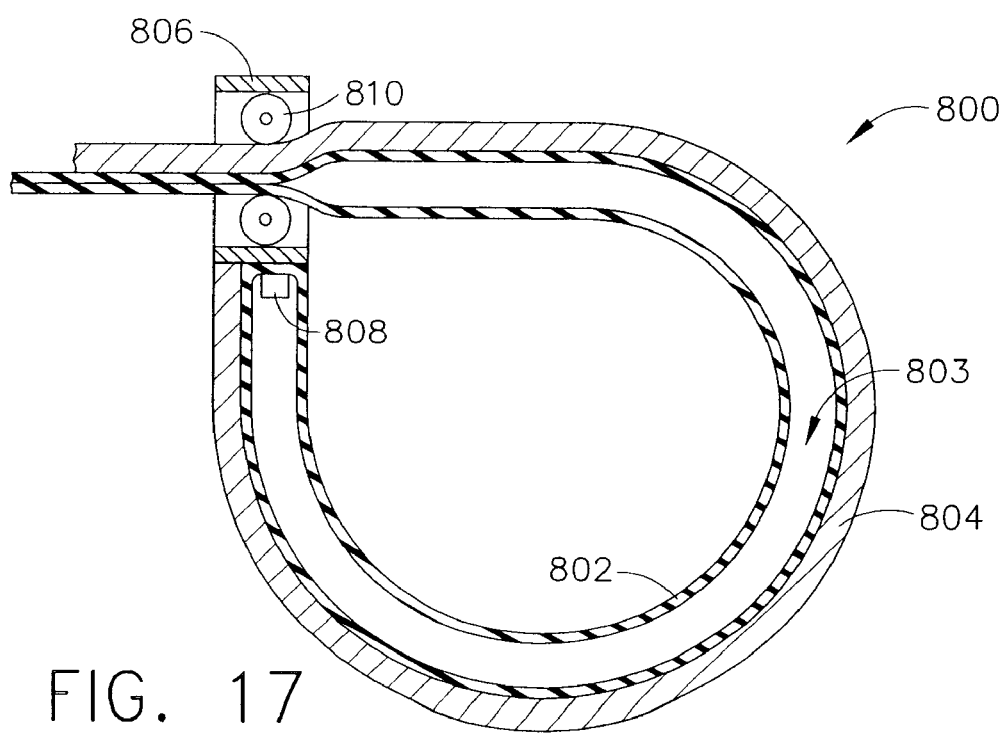
FIG. 17 is a partial, cross-sectional side view of yet another exemplary gastric band, with a pressure sensor.
Figure 18:
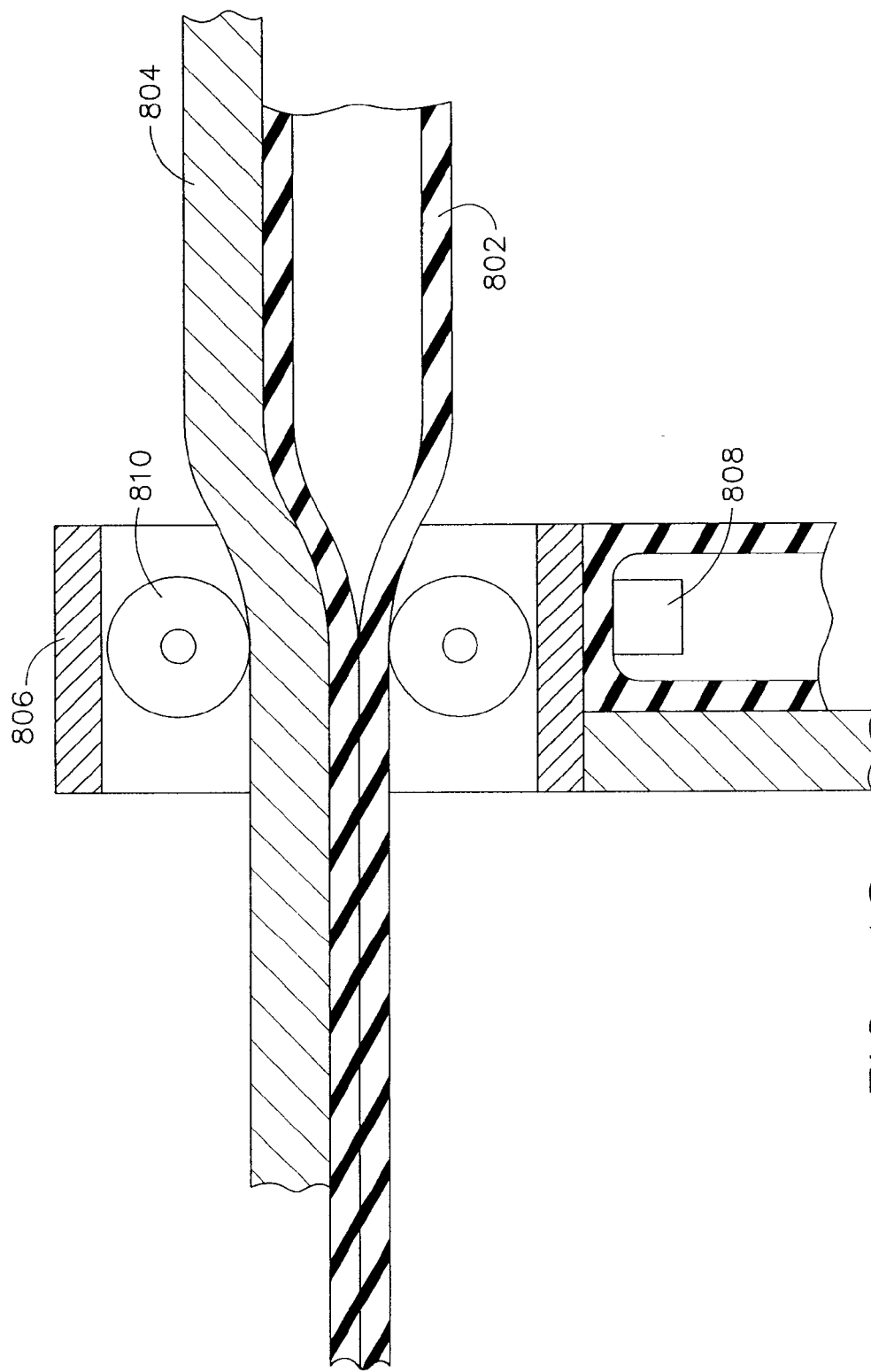
FIG. 18 is an enlarged partial cross-sectional side view of an adjustment portion of the gastric band of FIG. 17.

FIGS. 17-18 show yet another embodiment of a gastric band 800. In this embodiment, gastric band 800 comprises a bladder 802, a band 804, and a latch mechanism 806. Bladder 802 and band 804 are secured adjacent one another, such as by an adhesive. Bladder 802 and band 804 may each be formed of silicon or any other suitable material(s), including combinations thereof. One end of bladder 802 is fixedly secured to a latch mechanism 806, while the other end of bladder 802 is passed through latch mechanism 806 and may be adjusted relative to latch mechanism 806 to obtain a desired inner diameter defined by band 802. Similarly, one end of band 804 is fixedly secured to a latch mechanism 806, while the other end of band 804 is passed through latch mechanism 806 and may be adjusted relative to latch mechanism 806. Latch mechanism 806 is configured such that, when bladder 802 and band 804 are adjusted to provide a desired inner diameter, latch mechanism 806 is operable to secure the position of bladder 802 and band 804 relative to latch mechanism 806. Suitable mechanisms or features for providing such securing by latch mechanism 806 will be apparent to those of ordinary skill in the art. Similarly, suitable mechanisms or features for adjusting the position of the free end of bladder 802 and band 804 relative to latch mechanism 806 will be apparent to those of ordinary skill in the art.

Bladder 802 defines a vessel 803 holding a fluid (e.g., saline, etc.) and a pressure sensor 808. While pressure sensor 808 is shown as being located at an end of vessel 803, it will be appreciated that pressure sensor 808 may positioned in any other suitable location within vessel 803 or elsewhere. In the present example, pressure sensor 808 is operable to sense the pressure of the fluid within vessel 803. Pressure sensor 808 may be configured to communicate pressure data in a manner similar to communication of data by any other type sensor described herein. For instance, pressure sensor 808 may communicate pressure data to an external device using direct telemetry, using telemetry via an implanted data relay, or using any other suitable technique. In addition or in the alternative, pressure sensor 808 may communicate data to another implanted device, which may then process the pressure data for any suitable purpose.

FIG. 17 shows bladder 802 and band 804 in an extended configuration, providing a relatively large inner diameter. Latch mechanism 806 of this example comprises a pair of rollers 810. Bladder 802 and band 804 pass between rollers 810 such that rollers 810 squeeze bladder 802. In particular, bladder 802, band 804, and rollers 810 are configured such that fluid in vessel 803 is forced out of whatever portion of vessel 803 passes rollers 810 as bladder 802 and band 804 are pulled further through latch mechanism 806. In other words, the volume of vessel 803 will decrease as bladder 802 and band 804 are pulled further through latch mechanism 806. With a fixed amount of fluid being within vessel 803, it will be appreciated that a decrease in vessel 803 volume will cause an increase in the pressure of the fluid within vessel 803.

Accordingly, the pressure of fluid within vessel 803 will increase as the inner diameter defined by bladder 802 decreases. Similarly, if the inner diameter defined by bladder 802 is increased (e.g., by pushing bladder 802 back through latch mechanism 806), the volume of vessel 803 will increase, causing a decrease in the pressure of fluid within vessel 803. Such changes in pressure may be detected by pressure sensor 808 and communicated as described above.

In one embodiment, rollers 810 are passive. In other words, rollers 810 are configured to rotate freely, and some other mechanism provides movement of bladder 802 and band 804 relative to latch mechanism 806. Suitable mechanisms for providing movement of bladder 802 and band 804 relative to latch mechanism 806 will be apparent to those of ordinary skill in the art. In another embodiment, rollers 810 are active. In this embodiment, rollers 810 are powered (e.g., by a motor, etc.), and are operable to drive bladder 802 and band 804 through latch mechanism 806. Rollers 810 of this embodiment may have a high coefficient of friction or other properties. Of course, rollers 810 in this example are merely illustrative, and any other components or features may be used to squeeze bladder 802, drive bladder 802 and band 804 through latch mechanism 806, and/or serve other purposes. Other variations of gastric band 800, including variations of its components, uses, and principles of operation, will be apparent to those of ordinary skill in the art.

Each of the foregoing examples of a gastric band 10 include versions that are mechanically adjustable. As used herein, the term "mechanically adjustable" shall be read to include gastric bands 10 or other devices that define an inner diameter (e.g., to form a restriction in a patient) that is adjustable by movement of at least one non-inflating component (e.g., an actuator 150, a cable 222, a band 62, a band 602, a band 702, rollers 810, etc.). Such devices may be contrasted with those whose adjustments are provided merely by expansion or contraction of a fluid-filled member, with no movement of some other component, such as a conventional inflatable gastric band. While the above embodiments are described explicitly in the context of mechanically adjustable devices, it will be appreciated that the embodiments may be varied to include devices that are not mechanically adjustable.

As mentioned above, components of embodiments described herein may be made of non-ferromagnetic materials, allowing the patient to under go Magnetic Resonance Imaging (MRI) without damage to the device or patient. Being MRI safe may avoid limiting the medical procedures which are safely available to patients having implanted bands, etc. Alternatively, components may be made of any other suitable materials.

In addition to use during adjustments, the sensing systems of the foregoing examples may also be used to measure pressure variations, or variations of other parameters, in or a band 10 at various intervals during treatment. Periodic parameter readings may enable the sensing system to function as a diagnostic tool, to ensure that band 10 is operating effectively. In particular, a sensing system may be utilized to detect a no pressure condition associated with band 10, which may indicate a break or other condition. Alternatively, the system may be used to detect excessive pressure spikes associated with band 10, which may indicate a blockage within the stoma or other conditions.

It will become readily apparent to those skilled in the art that the above invention has equally applicability to other types of implantable bands. For example, bands are used for the treatment of fecal incontinence. One such band is described in U.S. Pat. No. 6,461,292 which is hereby incorporated herein by reference. Bands can also be used to treat urinary incontinence. One such band is described in U.S. Patent Application 2003/0105385 which is hereby incorporated herein by reference. Bands can also be used to treat heartburn and/or acid reflux. One such band is described in U.S. Pat. No. 6,470,892 which is hereby incorporated herein by reference. Bands can also be used to treat impotence. One such band is described in U.S. Patent Application 2003/0114729 which is hereby incorporated herein by reference.

The present invention has application in conventional endoscopic and open surgical instrumentation as well as application in robotic-assisted surgery.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. the sealed container may keep the instrument sterile until it is opened in a medical facility. A device may also be sterilized using any other technique known in the art, including but not limited to beta or gamma radiation, ethylene oxide, or steam.

While the present invention has been illustrated by description of several embodiments, it is not the intention of the applicant to restrict or limit the spirit and scope of the appended claims to such detail. Numerous other variations, changes, and substitutions will occur to those skilled in the art without departing from the scope of the invention. For instance, the device and method of the present invention has been illustrated in relation to providing the pressure sensor within the injection port. Alternatively, the sensor could be positioned within a fluid filled portion of the band in order to measure pressure changes within the band. Additionally, the pressure sensor could be associated with an elastomeric balloon implanted within the stomach cavity to measure fluid pressure within the balloon. The structure of each element associated with the present invention can be alternatively described as a means for providing the function performed by the element. It will be understood that the foregoing description is provided by way of example, and that other modifications may occur to those skilled in the art without departing from the scope and spirit of the appended Claims.

What is claimed is:

1. An apparatus for forming a restriction, the apparatus comprising:
    (a) an implantable mechanically adjustable band having a first end and a second end and configured to form a restriction in a patient, wherein the mechanically adjustable band defines an inner diameter, wherein the mechanical adjustability of the mechanically adjustable band is configured to permit the inner diameter defined by the band to be selectively varied;
    (b) an attachment mechanism configured to join the first end and the second end;
    (c) a bladder connected to the band, wherein the bladder is configured to be flexible yet substantially non-tensile;
    (d) an adjustment mechanism in communication with the mechanically adjustable band, wherein the adjustment mechanism comprises a first actuation portion and a second actuation portion, wherein the first actuation portion and the second actuation portion are in communication with the bladder, wherein the adjustment mechanism further comprises a latch mechanism comprising a pair of rollers defining a gap between the rollers, wherein the first actuation portion is operable to move in first and second directions relative to the second actuation portion, wherein the second actuation portion is configured to remain in a substantially constant spatial position as the first actuation portion moves in first and second directions, wherein the gap is sized such that the rollers squeeze the bladder as the bladder passes through the gap to adjust the inner diameter defined by the band after the first end and the second end of the band have been joined; and
    (e) a sensor in communication with one or both of the mechanically adjustable band or the adjustment mechanism, wherein the sensor is configured to sense a physical parameter associated with operation of the mechanically adjustable band, wherein the physical parameter varies with the inner diameter defined by the mechanically adjustable band.

2. The apparatus of claim 1, wherein the band and the bladder form a gastric band, wherein the gastric band is configured to fit around a portion of a patient's stomach.

3. The apparatus of claim 1, wherein the sensor comprises a proximity sensor.

4. The apparatus of claim 1, wherein the sensor comprises a force sensor.

5. The apparatus of claim 1, wherein the sensor comprises a linear displacement sensor.

6. The apparatus of claim 1, wherein the sensor comprises a pressure sensor.

7. The apparatus of claim 6, wherein the pressure sensor is positioned within the inner diameter defined by the band.

8. The apparatus of claim 7, further comprising a pressure sensing strip secured to the band, wherein the pressure sensor is provided on or in the pressure sensing strip.

9. The apparatus of claim 8, wherein the pressure sensing strip comprises a plurality of pressure sensors.

10. The apparatus of claim 6, wherein the bladder comprises a fluid filled member, wherein the pressure sensor is positioned within the fluid filled member to sense the pressure of fluid within the fluid filled member, wherein the pressure of fluid within the fluid filled member varies with the inner diameter defined by the band.

11. The apparatus of claim 10, wherein the fluid filled member comprises a vessel defining a volume, wherein the fluid filled member is configured such that the vessel volume decreases as the inner diameter formed by the band decreases.

12. The apparatus of claim 1, wherein the adjustment mechanism further comprises an electric motor, wherein the sensor comprises a control logic configured to sense a current provided by the motor, wherein the control logic is further configured to convert the sensed current into torque provided by the motor.

13. The apparatus of claim 1, wherein the adjustment mechanism further comprises an actuator configured to expand or contract.

14. The apparatus of claim 1, wherein the adjustment mechanism further comprises a hydraulic actuator.

15. The apparatus of claim 1, wherein the adjustment mechanism further comprises a pinion.

16. The apparatus of claim 1, wherein the latch is operable to selectively secure the position of the band relative to the latch.

17. An apparatus for forming a restriction, the apparatus comprising:
    (a) an implantable mechanically adjustable band comprising a first engagement portion and a second engagement portion, wherein the band defines an inner diameter, wherein the band is configured to fit around an anatomical structure in a patient, wherein the first engagement portion defines an opening extending therethrough, wherein the second portion is configured to slidably move through the opening;
    (b) a bladder connected to the band, wherein the bladder is configured to be flexible yet substantially non-tensile, wherein the bladder is in communication with the first engagement portion and the second engagement portion;
    (c) a mechanical actuator in communication with the second engagement portion, wherein the mechanical actuator comprises a latch mechanism having a pair of rollers defining a gap between the rollers, wherein the mechanical actuator is configured to move the second engagement portion through the gap, wherein the gap is sized such that the rollers squeeze the bladder as the bladder passes through the gap to adjust the inner diameter defined by the band; and (d) a sensor, wherein the sensor is configured to sense a parameter associated with operation of the band, wherein the sensed parameter pressure varies with the inner diameter defined by the band.

18. The apparatus of claim 17, wherein the sensor is located proximate to the band.

19. An apparatus for forming a restriction, the apparatus comprising:

(a) an implantable mechanically adjustable band, wherein the band defines an inner diameter, wherein the band is configured to fit around an anatomical structure in a patient;

(b) a bladder connected to the band, wherein the bladder is configured to be flexible yet substantially non-tensile;

(c) an adjustment mechanism comprising a latch mechanism, wherein the adjustment mechanism is operable to permit selective adjustment of the inner diameter defined by the band, wherein the adjustment mechanism is further configured to maintain a selected inner diameter defined by the band, wherein the latch mechanism comprises a pair of rollers defining a gap between the rollers, wherein the adjustment mechanism is operable to selectively drive the band and the bladder in first and second directions through the gap, wherein the gap is sized such that the rollers squeeze the bladder as the bladder passes through the gap;

(d) a sensor, wherein the sensor is configured to sense a parameter associated with operation of the band, wherein the sensed parameter varies with the inner diameter defined by the band.

* * * * *